(12) United States Patent
Vanfleteren et al.

(10) Patent No.: US 11,740,229 B2
(45) Date of Patent: Aug. 29, 2023

(54) METHOD AND SYSTEM FOR DETERMINING BIOMARKER CONCENTRATION

(71) Applicants: UNIVERSITEIT GENT, Ghent (BE); IMEC VZW, Leuven (BE)

(72) Inventors: Jan Vanfleteren, Gentbrugge (BE); Patricia Khashayar, Ghent (BE)

(73) Assignees: UNIVERSITEIT GENT, Ghent (BE); IMEC VZW, Leuven (BE)

(*) Notice: Subject to any disclaimer, the term of this patent is extended or adjusted under 35 U.S.C. 154(b) by 1004 days.

(21) Appl. No.: 16/482,962

(22) PCT Filed: Jan. 26, 2018

(86) PCT No.: PCT/EP2018/051969
§ 371 (c)(1),
(2) Date: Aug. 1, 2019

(87) PCT Pub. No.: WO2018/141645
PCT Pub. Date: Aug. 9, 2018

(65) Prior Publication Data
US 2020/0232968 A1     Jul. 23, 2020

(30) Foreign Application Priority Data

Feb. 1, 2017   (EP) .................................. 17154242

(51) Int. Cl.
*G01N 33/49*     (2006.01)
*G01N 27/06*     (2006.01)
*G01N 33/487*    (2006.01)

(52) U.S. Cl.
CPC ........... *G01N 33/492* (2013.01); *G01N 27/06* (2013.01); *G01N 33/48707* (2013.01)

(58) Field of Classification Search
CPC . G01N 33/492; G01N 27/06; G01N 33/48707
See application file for complete search history.

(56) References Cited

U.S. PATENT DOCUMENTS

| 6,330,819 | B1 | 12/2001 | Yang |
| 2011/0155589 | A1 | 6/2011 | Chatelier et al. |
| 2017/0010259 | A1 | 1/2017 | Amoabediny et al. |

FOREIGN PATENT DOCUMENTS

WO   2008141076 A1   11/2008

OTHER PUBLICATIONS

Liu, Xiaoqiang, and Danny KY Wong. "Picogram-detection of estradiol at an electrochemical immunosensor with a gold nanoparticle | Protein G-(LC-SPDP)-scaffold." Talanta 77.4 (2009): 1437-1443. (Year: 2009).*

(Continued)

*Primary Examiner* — Robert J Eom
(74) *Attorney, Agent, or Firm* — WORKMAN NYDEGGER

(57) ABSTRACT

A method for deriving a calibration curve for determining a concentration of an analyte in an electrochemical reactor comprises determining a current level between a functionalized electrode and a reference electrode in the electrochemical reactor in absence of an analyte, the current level forming a zero-concentration current; injecting a fluid comprising an analyte in a first given concentration in the electrochemical reactor, determining after the predetermined amount of time a first calibration current level corresponding to the first given concentration and calculating a first current ratio of the first current level to the zero-concentration current; repeating the previous step for at least a second given concentration of the analyte, yielding at least a second current ratio of a second current level to the zero-concentration current; obtaining a calibration curve indicative of current ratio as a function of concentration from the first current ratio and at least the second current ratio.

17 Claims, 4 Drawing Sheets

(56) References Cited

OTHER PUBLICATIONS

Pereira, Sirley V., et al. "A microfluidic device based on a screen-printed carbon electrode with electrodeposited gold nanoparticles for the detection of IgG anti-Trypanosoma cruzi antibodies." Analyst 136.22 (2011): 4745-4751. (Year: 2011).*

Yun, Yeo-Heung, et al. "A label-free electronic biosensor for detection of bone turnover markers." Sensors 9.10 (2009): 7957-7969. (Year: 2009).*

May, Jennifer E., et al. "Use of whole blood for analysis of disease-associated biomarkers." Analytical biochemistry 437.1 (2013): 59-61. (Year: 2013).*

European Search Report from EP Application No. 17154242, dated May 23, 2017.

International Search Report from PCT Application No. PCT/EP2018/051969, dated Feb. 12, 2018.

* cited by examiner

METHOD AND SYSTEM FOR DETERMINING BIOMARKER CONCENTRATION

FIELD OF THE INVENTION

The present invention is generally related to the field of measurement techniques and systems for determining biomarker concentration in a body fluid.

BACKGROUND OF THE INVENTION

The use of electrochemical microfluidic reactors has been studied for use in a variety of applications. In analytical applications micro-electrochemical reactors can provide for measurement of small quantities or concentrations of an analyte.

For example, electrochemical reactions have been used to provide for pumping liquids within microfluidic systems for applications such as drug delivery, chemical blood analysis and flow cytometry.

In a more particular example microfluidic reactors can be used for measuring concentrations of a bone turnover marker (BTM). In such a measurement procedure Au electrodes are functionalised with Au nanoparticles and antibody complex immobilized on the electrode surface. The functionalised electrodes are exposed to the (liquid) analyte, containing a certain (to be determined) concentration of BTMs. Specific BTMs (i.e. proteins like osteocalcin, P1NP, CTX) bind with their dedicated/matching antibodies. The BTM containing analyte is removed from the reactor. Subsequently a detection solution is injected in the reactor and a voltage is applied between working and reference electrode, causing an electrical current flow, of which the intensity depends on the BTM concentration, which was present in the analyte, and which determines how much BTM per unit area is bound to the available antibodies. The higher the BTM concentration, the more BTMs are bound, the smaller is the amount of free antibodies on the electrode surface, and, as the antibodies provide a conducting path for the current, the smaller the measured current is. This decrease relies on the fact that the redox probe present in the solution is denied access to the electrode surface upon binding of the substrate to a surface-confined receptor, here antibody and antigen, and thus reduced electron transfer occurs and a reduced amount of current is read.

In chronoamperometry the current flowing from working to reference electrode is measured as a function of time (t). Current measurement is started (t=0) at the moment that voltage is applied. Normally a decreasing current in function of time is seen, stabilising after a certain time (usually in the order of seconds). The stabilised current intensity I is recorded (e.g. at t=10 s). Schematically a typical chronoamperometric recording looks like in FIG. 1.

Due to non-reproducible Au nanoparticle and/or antibodies functionalisation and/or due to ageing effects of the functionalised reactors, measured current intensities on identical reactors with identical BTM concentrations can vary a lot (currently up to a factor of 10). This means that chronoamperometry using absolute current intensity measurements cannot be used for determining BTM concentrations. Further, electrodes in different batches may have somewhat different features, e.g. a difference in thickness, which also contribute to the non-reproducibility.

Hence, there is a need for a procedure to measure a concentration of an analyte in a precise and reproducible way and independently of properties of individual electrochemical reactors and the electrodes used therein.

SUMMARY OF THE INVENTION

It is an object of embodiments of the present invention to provide for a method for determining a calibration curve for determining a concentration of an analyte in a reactor. It is also an object to provide a method for measuring an unknown concentration using said calibration curve.

The above objective is accomplished by the solution according to the present invention.

In a first aspect the invention relates to a method for deriving a calibration curve for determining a concentration of an analyte in an electrochemical reactor. The method comprises:

determining a current level measured after a predetermined amount of time between a functionalised electrode and a reference electrode in the electrochemical reactor in absence of an analyte, said current level forming a zero-concentration current, injecting a fluid comprising an analyte in a first given concentration in said electrochemical reactor, determining after said predetermined amount of time a first calibration current level corresponding to said first given concentration and calculating a first current ratio of said first current level to said zero-concentration current, repeating the previous step for at least a second given concentration of said analyte, yielding at least a second current ratio of a second current level to said zero-concentration current, obtaining a calibration curve indicative of current ratio as a function of concentration from said first current ratio and at least said second current ratio.

The proposed solution indeed allows for obtaining a calibration curve which can subsequently be used for measuring in a reproducible way a concentration of an analyte in a fluid. As the calibration curve is derived by means of current ratios, which are found to be constant when measuring concentrations over various electrochemical reactors, one so indeed obtains a tool for performing concentration measurements in a repeatable way, which was not possible in the state of the art.

In one embodiment another electrochemical reactor is used in said step of repeating, said other electrochemical reactor having substantially a same design as the electrochemical reactor used when determining said first current ratio, and a current level forming a zero-concentration current is determined for that other electrochemical reactor and the analyte of said at least second concentration is injected in that other electrochemical reactor.

In another aspect the invention relates to a method for determining an unknown concentration of an analyte, comprising deriving a calibration curve with the method as set out above, taking a further electrochemical reactor having the same design as the electrochemical reactor used when determining said calibration curve, determining a current level measured after the predetermined amount of time between a functionalised electrode and a reference electrode in that further electrochemical reactor in absence of an analyte, said current level forming a zero-concentration current, injecting the fluid comprising the analyte in an unknown concentration in the further electrochemical reactor, determining after the predetermined amount of time a current value corresponding to the unknown concentration, calculating a current ratio of the current value to the zero-concentration current obtained in the previous step, and determining the unknown concentration using the calibration curve and the current ratio corresponding to the unknown concentration.

The invention indeed allows, thanks to the calibration curve derived as described above, determining an unknown concentration of the analyte in the fluid. Similar steps as before are performed to obtain a zero concentration current and a current value in accordance with the unknown concentration. Again the property is then relied on that current ratios are constant when measuring over various electrochemical reactors for specific concentrations of a certain analyte.

In a preferred embodiment the electrochemical reactor is a microfluidic reactor.

In a typical embodiment a detection solution is injected for determining the current level.

In certain embodiments the functionalised electrode comprises Au, nanoparticles and antibody complexes.

In one embodiment the analyte is biomarker. In a specific embodiment it is a bone turnover marker, like e.g. Osteocalcin (Oc) and cross-linked C-telopeptide of type I collagen (CTX).

In a preferred embodiment the fluid is a body fluid, for example whole blood, saliva or urine.

The invention also relates to a measurement system for carrying out the above-described method.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The above and other aspects of the invention will be apparent from and elucidated with reference to the embodiment(s) described hereinafter.

BRIEF DESCRIPTION OF THE DRAWINGS

The invention will now be described further, by way of example, with reference to the accompanying drawings, wherein like reference numerals refer to like elements in the various figures.

DETAILED DESCRIPTION OF ILLUSTRATIVE EMBODIMENTS

Figure 1:
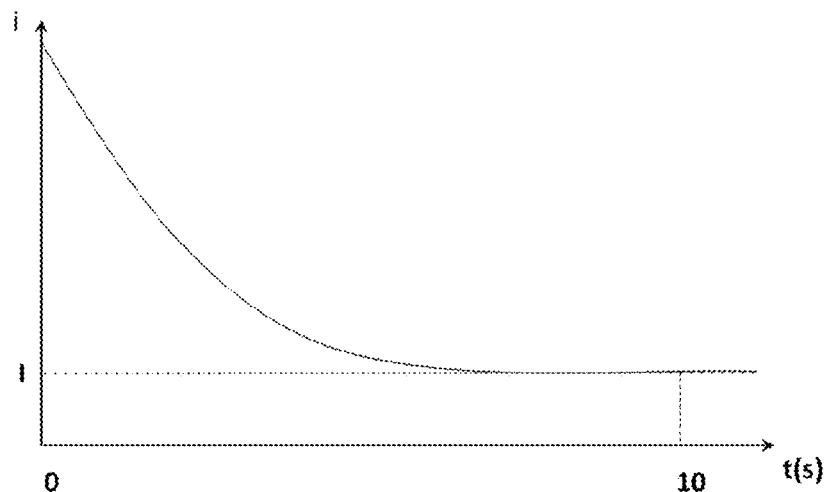
FIG. 1 illustrates a typical shape of a chronoamperometric recording.

The present invention will be described with respect to particular embodiments and with reference to certain drawings but the invention is not limited thereto but only by the claims.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

It should be noted that the use of particular terminology when describing certain features or aspects of the invention should not be taken to imply that the terminology is being re-defined herein to be restricted to include any specific characteristics of the features or aspects of the invention with which that terminology is associated.

In the description provided herein, numerous specific details are set forth. However, it is understood that embodiments of the invention may be practiced without these specific details. In other instances, well-known methods, structures and techniques have not been shown in detail in order not to obscure an understanding of this description.

The present invention discloses a method for determining a concentration of different biomarkers in body fluids (e.g. blood, urine, saliva) and a measurement system to carry out the method.

The invention capitalizes on the observation that the available electrochemical reactors display the property that the ratio of current intensities measured for different concentrations of analyte (e.g. BTM) is constant over different reactors. To be more precise: if $I_{Rm,Ci}$ is the measured current intensity in reactor m for an analyte concentration $C_i$, then $$\frac{I_{Rm,Ci}}{I_{Rm,Cj}} = \frac{I_{Rn,Ci}}{I_{Rn,Cj}} \quad (1)$$

where normally, as mentioned above, for two reactors Rm and Rn holds $$I_{Rm,Ci} \neq I_{Rn,Ci}$$

This property (1) is exploited to propose a precise measurement procedure of analyte concentrations, which does not depend on the (varying) current level and/or sensitivity properties of the individual reactors.

An embodiment of the method for deriving a calibration curve for determining a concentration of an analyte in an electrochemical reactor according to the present invention, is now discussed in detail.

The method aims to calibrate a reactor with a certain, given design (hence, with known dimensions and electrical and fluidic properties) using analytes with known concentrations. In the example used in the explanation below a bone turnover marker is taken as analyte.

First baseline current measurements are performed. One starts from a reactor with functionalised electrodes (comprising e.g. Au, nanoparticles and antibodies). The electrodes have a known design and are always used in a fixed set-up, i.e. parameters like electrode size and nature, interdistance, applied materials, used detection probe, device set-up (e.g. microfluidic or not), . . . are well-known and remain unchanged. No analyte is injected, so no markers are bound to antibodies and currents are measured for an analyte concentration equal to 0. A detection solution is injected (e.g. 1 mM K3[Fe(CN)6] in case BTM is used as analyte) and a voltage (e.g. 0.65 V) is applied between the reference electrode and the working electrode. Then chronoamperometry is performed, i.e. the current at the working electrode is recorded as a function of time. The calibration current $I_{CAL,0}$ is determined for this analyte concentration (=0). This determination is done a given amount of time after the voltage had been applied or longer. What counts is that a stable current level has been reached.

Next a current measurement is performed for a known calibration concentration $C_{CAL,1}$. One starts from the reactor used in the preceding step. The measurement is performed after the baseline current measurement, but before the properties of the functionalized surface have changed. The detection solution of the baseline measurement has to be removed first, by flushing/washing with a buffer solution. A calibration solution is injected with in this case pure antigen of corresponding BTM of known concentration $C_{CAL,1}$. After an incubation time the BTM or antigen binds with the antibodies on the reactor electrodes. Next the calibration solution is washed away with a buffer solution. From then on, the same procedure is adopted as during the baseline current measurement: the detection solution is injected, a voltage is applied and chronoamperometry is performed, which yields the calibration current $I_{CAL,1}$ for concentration $C_{CAL,1}$.

The measurements of the calibration current at zero concentration and at known concentration $C_{CAL,1}$ yield a first calibration value $R_{CAL,1}$, which is the ratio of the two currents:

$$R_{CAL,1} = \frac{I_{CAL,1}}{I_{CAL,0}} \quad (2)$$

The above described procedure is then repeated for a plurality of concentrations $C_{CAL,i}$ (i=2 . . . N) which are representative for possible test samples containing actual analyte concentrations to be determined. In this way N different calibration values $R_{CAL,1}, \ldots, R_{CAL,i}, \ldots, R_{CAL,N}$ are determined:

$$R_{CAL,i} = \frac{I_{Ri,CAL,i}}{I_{Ri,CAL,0}} \quad (i = 1, \ldots, N) \quad (3)$$

wherein $I_{Ri,CAL,0}$ and $I_{Ri,CAL,i}$ denote the baseline current and the calibration current measured for concentration $C_{CAL,i}$ using reactor $R_i$, respectively. In a preferred embodiment a fresh reactor is used for each calibration value determination. As mentioned before, baseline currents $I_{Ri,CAL,0}$ for different reactors $R_i$ normally vary quite widely. For each reactor $R_i$ the baseline current $I_{Ri,CAL,0}$ needs to be measured. In order to obtain reliable measurements it is important that the various reactors $R_i$ have substantially the same design. Most preferably they are identical to one another. However, minor deviations in the design from one reactor to another may be acceptable. In an alternative embodiment a single reactor is used for all calibration measurements. In the latter case the procedure set out above for the current measurement for a known calibration concentration (starting from the removal of the detection solution) and for calculating the current ratio is repeated using the same reactor. This can be done only if calibration samples with increasing concentrations are used. In this case, obviously, only one baseline current measurement is necessary for the whole calibration measurement procedure.

Figure 2:
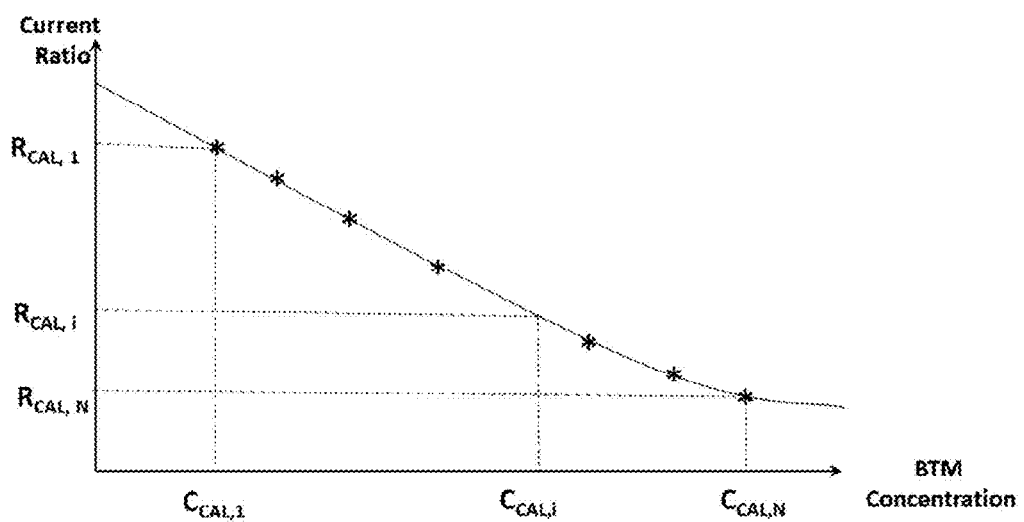
FIG. 2 illustrates a typical shape of a calibration curve.

The concentration range of the calibration sample collection is preferably large enough to include any possible actual test sample concentration. Plotting the different values of calculated current ratios $R_{CAL,i}$ versus calibration concentrations $C_{CAL,i}$ yields with conventional fitting techniques the calibration curve (with a typical shape as illustrated in FIG. 2) which is characteristic for this particular type of reactor, i.e. a reactor with the given fixed design, testing this particular type of analyte.

In principle the calibration curve needs to be determined only once for each type of reactor and analyte, e.g. in the lab, using calibration samples with known analyte concentrations. This means that each type of reactor comes with a particular calibration curve for each type of analyte to be tested with this reactor type. The calibration curve can then be used for determination of unknown analyte concentrations in actual test samples.

Although in the above explanation chronoamperometry is applied, it should be noted that in other embodiments other electrochemical detection such as differential pulse voltammetry can be used with the proposed method.

Figure 3:
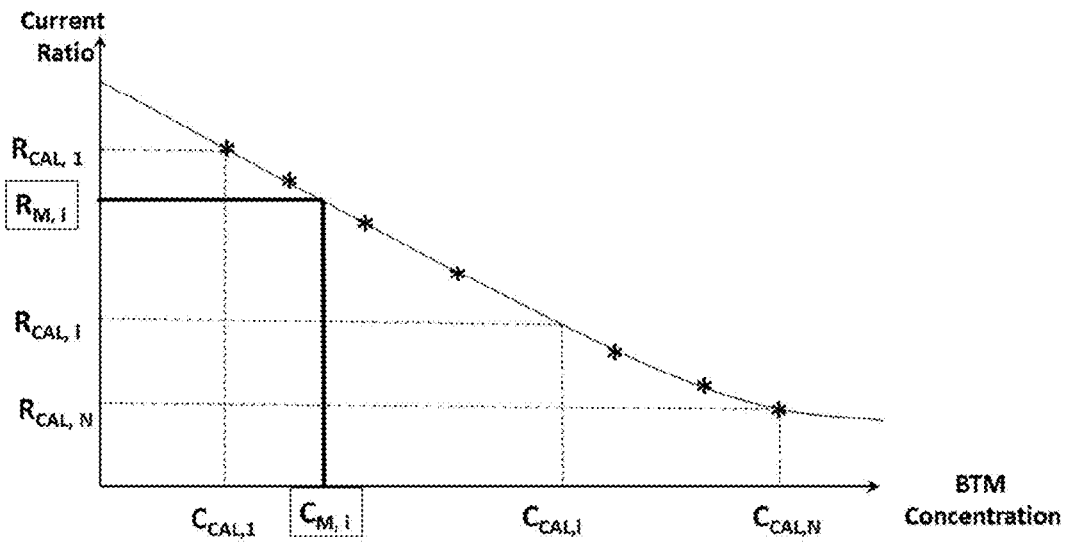
FIG. 3 illustrates the use of the calibration curve when determining an unknown concentration of analyte.

In order to measure unknown BTM concentrations, the following procedure is adopted. One starts from a reactor with substantially the same (and preferably exactly the same) design as the one for which the calibration curve has been obtained. Using this reactor a baseline current measurement is performed, in exactly the same way as described above. This yields the measurement baseline current $I_{M,0}$. Subsequently, and again in exactly the same way as previously explained, a current measurement is carried out for the sample i with the unknown analyte concentration. This yields the measurement sample current $I_{M,i}$. By dividing the two obtained current values the sample measurement current ratio $R_{M,i}$ can be calculated. By trend analysis using the trend of the reactor/BTM calibration curve at two points of the curve between which the new reading is located, the BTM concentration in the measurement sample $C_{M,i}$ can finally be determined. FIG. 3 provides an illustration of a typical curve.

To illustrate the method of the present invention some experimental results are now briefly described. In one experiment cyclic voltammetry electrodeposition is first used to coat the working electrode with a gold nanoparticle layer to improve the electron transfer rate and allow sufficient immobilization of antibodies (Abs) on the surface in later steps. In subsequent steps the gold surface is modified for capturing antibodies that, during the assay, bind specifically to the analyte molecules (antigens). In this regard, the Abs are immobilized on the treated surface through covalent binding using cross linkers. The electrodes are first activated by injecting an aqueous solution of 10 mM GSH (glutathione) and leaving to incubate for one hour. As the next step, the antibody complex is introduced to the electrode. The sample is then allowed to incubate for two hours on the sensor electrodes. The antibody complex is prepared by incubating the antibodies with cross-linkers (100 mM N-hydroxysulfosuccinimide (s-NHS) for Oc, 400 mM 1-ethyl-3-(3-dimethylaminopropyl)carbodiimide hydrochloride (EDC)/100 mM s-NHS for CTX) for 2.5 hours at room temperature. The cross-linkers provide covalent attractions between the constituents, facilitating the bonding of the primary amine groups (—NH2) of the antibody to the carboxylic group of GSH to form stable amide bonds. The electrode is washed between each step with DI to remove unbound fractions. 0.2% (w/v) BSA solution in PBS buffer is then introduced to the treated electrode for one hour to block unreacted active functional groups. Finally it is rinsed with PBS and then with PBS-Tween 20 thoroughly to remove unbound analytes and other non-specific entities from the electrode surface.

To investigate the applicability for osteoporosis care, electrochemical immunoassay is performed using fabricated device to measure serum levels of certain BTMs. All experiments are performed within a day to obtain a good sensitivity because the immobilized antibody (Ab) might be degenerated a few days after the electrochemical chip is fabricated.

For this purpose, different concentrations of Oc and CTX are applied on the electrode as the analytes for the sensing test and the chronoamperometric signals are recorded. The antibody-antigen reaction provides a redox current, which is interpreted by the chronoamperometry. A high quality signal is obtained at +0.65V in DPV testing, thus, this potential is taken as the best value for BTM determination.

In this regard, the electrodes are washed using PBS. Thereafter, the detection solution, $K_3[Fe(CN)_6]$, is applied for chronoamperometry measurements (0.1 mM $K_3[Fe(CN)_6]$ containing 0.01 M NACl solution, as a redox probe, potential of 0.65 V for 15 s). The measured current at 10 s (when the status in the microchannel was stabilized) is considered as baseline. Then again, the electrodes are washed using PBS. At this step, the desired antigen concentration is introduced to the electrodes and left to incubate for 5 minutes. After each measurement, a relatively large amount of buffer solution is used to wash the analyte sample out.

In this system the current ratio is calculated by dividing the current measured after incubating the electrode with the specific concentration of the antigen by the current measured from the same electrode after the Ab-functionalization process. Thereafter, the average of the ratios calculated from several electrodes incubated with certain antigen concentration is used to develop the calibration curves.

Figure 4A:
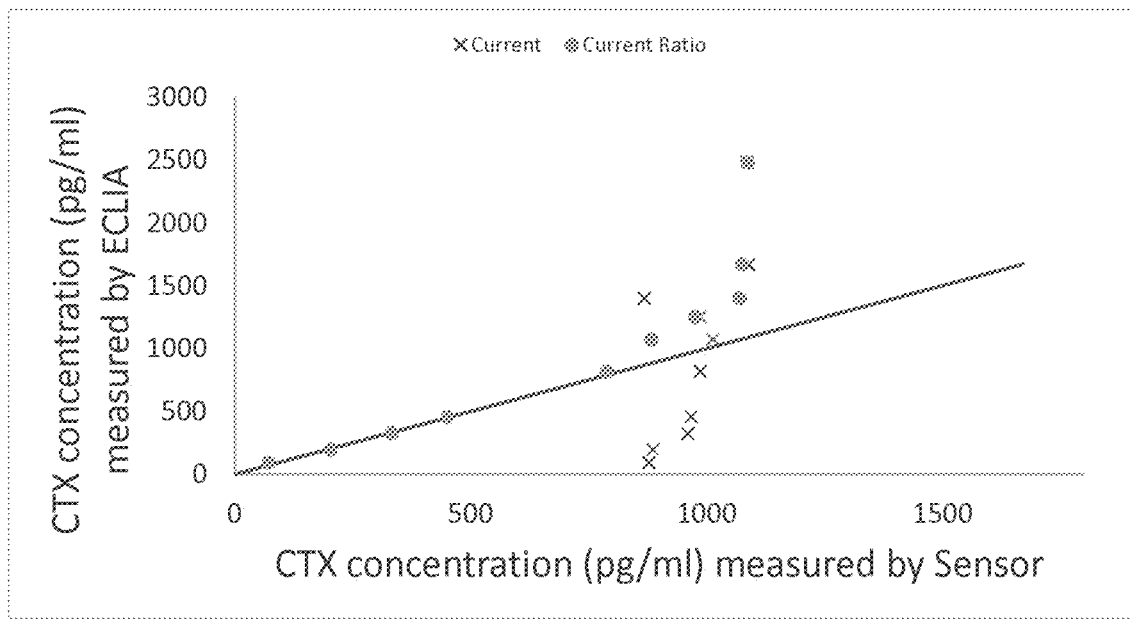
FIGS. 4a to 4d illustrate some measurement results.
Figure 4B:
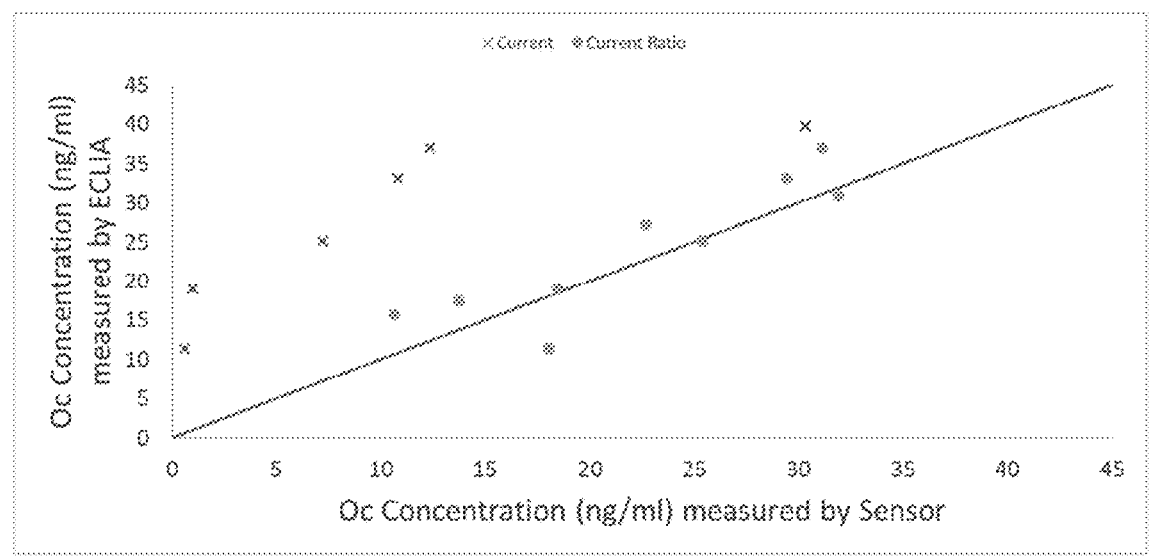
Figure 4C:
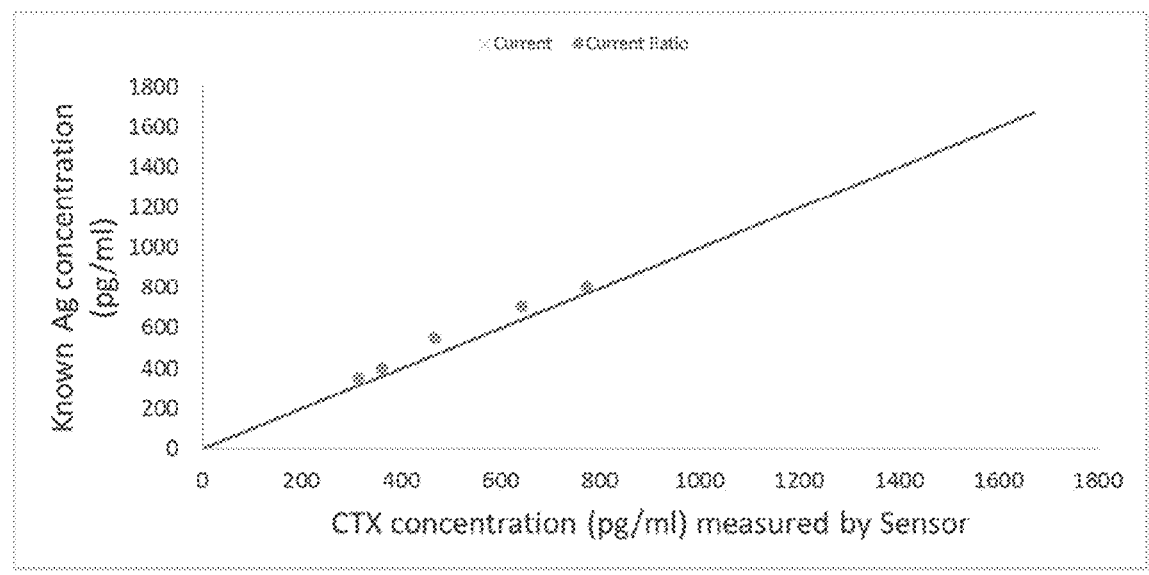
Figure 4D:
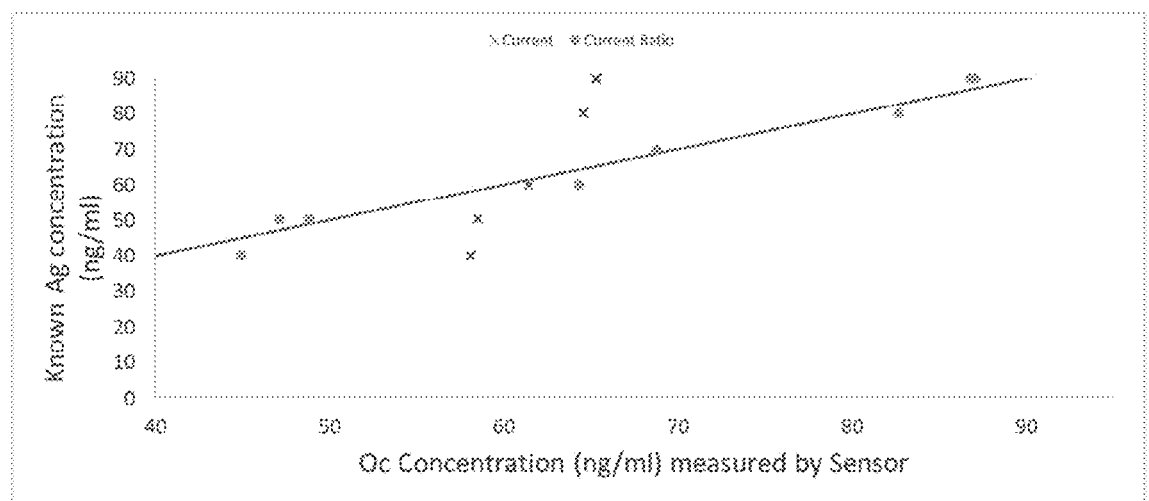

In FIGS. 4a to 4d, results of a series of measurements are shown making use of the calibration curves developed as described above. The read currents of the used sensor are fitted in the calibration curve in order to determine the concentration. In FIGS. 4c and 4d known concentrations of CTX and Oc antigens, respectively, are applied. A single electrode treated with antibody was exposed to increasing levels of the corresponding antigen. In brief, the surface was exposed to antigen and incubated for 5 minutes and then washed with a buffer. Thereafter, the measurement was performed as described above. Again the surface was washed and the next higher concentration of the antigen was applied and the whole process was repeated. In FIGS. 4a and 4b CTX and Oc levels in serum samples from patients were measured using our sensor and ECLIA (electrochemiluminescence, i.e. the current state of the art). The concentration calculated here was then compared with that reported by ECLIA. These numbers are plotted in FIG. 4a and FIG. 4b. The plots show that the compatibility is much higher when current ratio is used for the calibration curve and further measurements rather than average results.

While the invention has been illustrated and described in detail in the drawings and foregoing description, such illustration and description are to be considered illustrative or exemplary and not restrictive. The foregoing description details certain embodiments of the invention. It will be appreciated, however, that no matter how detailed the foregoing appears in text, the invention may be practiced in many ways. The invention is not limited to the disclosed embodiments.

Other variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method for deriving a calibration curve for determining a concentration of an analyte in an electrochemical reactor with a given design, the method comprising:

determining a current level, measured after a predetermined amount of time, between a functionalized electrode and a reference electrode in said electrochemical reactor in absence of an analyte, said current level forming a zero-concentration current, injecting a fluid comprising an analyte in a first given concentration in said electrochemical reactor, determining after said predetermined amount of time a first calibration current level corresponding to said first given concentration and calculating a first current ratio of said first current level to said zero-concentration current, repeating the previous step for at least a second given concentration of said analyte, yielding at least a second current ratio of a second current level to said zero-concentration current, obtaining a calibration curve indicative of current ratio as a function of concentration from said first current ratio and at least said second current ratio, said current ratio being constant for electrochemical reactors with the given design.

2. The method for deriving a calibration curve as in claim 1, wherein in said repeating another electrochemical reactor is used having the same design as the electrochemical reactor used when determining said first current ratio, and wherein a current level forming a zero-concentration current is determined for that other electrochemical reactor and said analyte of said at least second concentration is injected in that other electrochemical reactor.

3. The method as in claim 1, wherein before the current level determination a detection solution is injected.

4. The method as in claim 1, wherein said electrochemical reactor is a microfluidic reactor.

5. The method as in claim 1, wherein said functionalized electrode comprises Au, nanoparticles and antibody complexes.

6. The method as in claim 1, wherein said analyte is a biomarker.

7. The method as in claim 6, wherein said analyte is a bone turnover marker.

8. The method as in claim 1, wherein said fluid is a body fluid.

9. The method as in claim 8, wherein said body fluid is whole blood.

10. A method for determining an unknown concentration of an analyte, comprising:
deriving a calibration curve by
determining a current level, measured after a predetermined amount of time, between a functionalized electrode and a reference electrode in an electrochemical reactor with a given design in absence of an analyte, said current level forming a zero-concentration current, injecting a fluid comprising an analyte in a first given concentration in said electrochemical reactor, determining after said predetermined amount of time a first calibration current level corresponding to said first given concentration and calculating a first current ratio of said first current level to said zero-concentration current, repeating the previous step for at least a second given concentration of said analyte, yielding at least a second current ratio of a second current level to said zero-concentration current, obtaining a calibration curve indicative of current ratio as a function of concentration from said first current ratio and at least said second current ratio, said current ratio being constant for electrochemical reactors with the given design, taking a further electrochemical reactor having the same design as the electrochemical reactor used when determining said calibration curve, determining a current level measured after said predetermined amount of time between a functionalized electrode and a reference electrode in said further electrochemical reactor in absence of an analyte, said current level forming a zero-concentration current, injecting said fluid comprising said analyte in an unknown concentration in said further electrochemical reactor, determining after said predetermined amount of time a current value corresponding to said unknown concentration, calculating a current ratio of said current value to said zero-concentration current obtained in the previous step, and determining said unknown concentration using said calibration curve and said current ratio corresponding to said unknown concentration.

11. The method as in claim 10, wherein before a step of current level determination a detection solution is injected.

12. The method as in claim 10, wherein said electrochemical reactor is a microfluidic reactor.

13. The method as in claim 10, wherein said functionalized electrode comprises Au, nanoparticles and antibody complexes.

14. The method as in claim 10, wherein said analyte is a biomarker.

15. The method as in claim 14, wherein said analyte is a bone turnover marker.

16. The method as in claim 10, wherein said fluid is a body fluid.

17. The method as in claim 16, wherein said body fluid is whole blood.

* * * * *